United States Patent [19]

Tatakis

[11] Patent Number: 5,304,542
[45] Date of Patent: Apr. 19, 1994

[54] USE OF PLATELET FACTOR 4 TO INHIBIT OSTEOBLAST PROLIFERATION

[75] Inventor: Dimitris N. Tatakis, Louisville, Ky.

[73] Assignee: University of Louisville Research Foundation, Inc., Louisville, Ky.

[21] Appl. No.: 938,026

[22] Filed: Aug. 28, 1992

[51] Int. Cl.$^5$ .................. A61K 37/00; A61K 45/05
[52] U.S. Cl. .................. 514/12; 530/380; 530/824; 424/532; 424/85.2; 514/21
[58] Field of Search ............ 424/85.2, 532; 514/12, 514/21; 530/380, 829

[56] References Cited

U.S. PATENT DOCUMENTS

| | | | |
|---|---|---|---|
| 4,645,828 | 2/1987 | Twardzik et al. | 530/324 |
| 4,702,908 | 10/1987 | Thorbecke | 424/88 |
| 4,737,580 | 4/1988 | Twardzik et al. | 530/388 |
| 5,086,164 | 2/1992 | Maione | 530/324 |
| 5,112,946 | 5/1992 | Maione | 530/324 |
| 5,124,316 | 6/1992 | Antoniades et al. | 514/12 |
| 5,154,921 | 10/1992 | Sager et al. | 530/350 X |
| 5,185,323 | 2/1993 | Gewirtz | 514/12 |

FOREIGN PATENT DOCUMENTS

WO85/04397 10/1985 PCT Int'l Appl.

OTHER PUBLICATIONS

Canalis et al. *J. Clin. Invest.* 81:277–281 (1988).
Glowacki *Life Sciences* 33:1019–1024 (1983).
Wood *The New England Journal of Medicine* 327:620–627 (1992).
Rodan *Cancer Research* 47:4961–4966 (1987).
Sakamoto *Biochim. et Biophysica Acta* 385:41–50 (1975).
Horton *Biochim. et Biophysics Acta* 630:459–461 (1980).
Osterman *Biochem. Biophys. Res. Comm.* 107:130 (1981).
Hiti-Harper *Science* 199:991 (1978).
Deuel *Proc. Nat'l Acad. Sci USA* 78:4585 (1981).
Maione *Science* 247:77 (1989).
Rucinski *Thrombosis & Haematosis* 63:493 (1990).

*Primary Examiner*—Michael G. Wityshyn
*Assistant Examiner*—C. Sayala
*Attorney, Agent, or Firm*—Fish & Richardson

[57] ABSTRACT

The invention features a method for inhibiting proliferation of osteoblasts in a mammal in need of such inhibition. The method entails administering PF4. PF4 can be used to treat both diseases characterized by primary changes in osteoblastic cell function/activity (e.g., ossifying fibroma and fibrous dysplasia, osteoblastoma and osteoid osteoma, and osteosarcoma) and diseases or systemic conditions affecting bone in which abnormal osteoblastic cell function/activity is a secondary effect (e.g., acromegaly, hypercalcemia, primary or secondary hyperparathyroidism, hyperthyroidism, osteoporosis, or Paget's disease of bone). In addition, PF4 may be used to treat diseases associated with localized changes in bone metabolism in which abnormal osteoblastic cell function/activity contributes to pathogenic bone changes. For example, PF4 can be used to treat periodontal disease (localized, inflammation-induced bone loss), rheumatoid arthritis and osteoarthritis (localized, inflammation-induced bone loss) localized osteoporosis, mastocytosis, multiple myeloma, and bone metastases of various tumors. Because of its inhibitory effect on osteoblastic cell proliferation, PF4 can be used to treat bone abnormalities associated with either undesired osteoblastic cell proliferation or undesired osteoblastic cell function or activity.

8 Claims, 3 Drawing Sheets

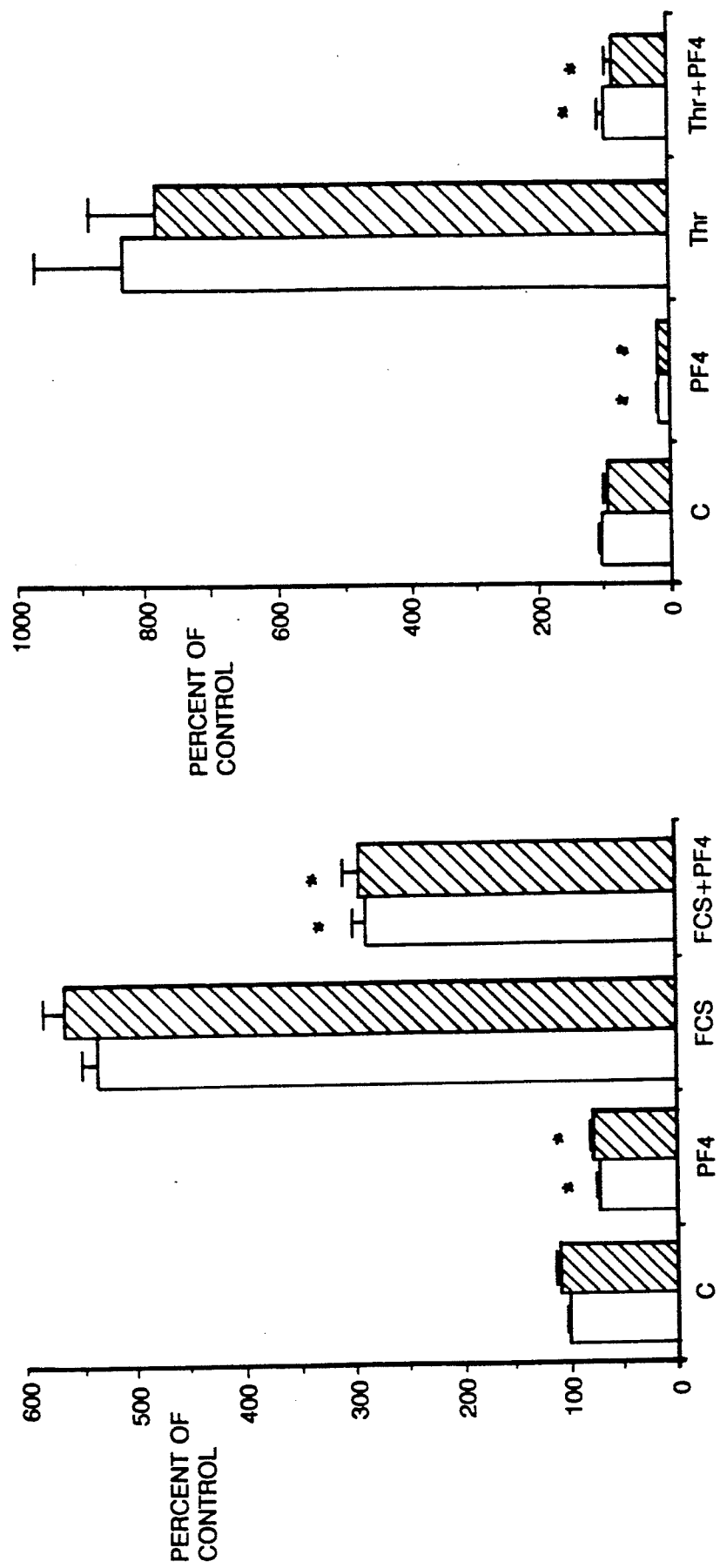

USE OF PLATELET FACTOR 4 TO INHIBIT OSTEOBLAST PROLIFERATION

STATEMENT AS TO FEDERALLY SPONSORED RESEARCH

This work was supported in part by NIH Grant No. DE09915 and the government has certain rights in the invention.

BACKGROUND OF THE INVENTION

Platelet factor 4 (PF4) is a well-known protein which has been completely sequenced (Deuel et al. Proc. Natl. Acad. Sci. USA 78:4585, 1981). It is a 70-residue secretable platelet protein with a molecular weight of approximately 7.8 Kd which is released during platelet aggregation.

PF4 possesses characteristic structural features of the pro-inflammatory proteins interleukin-8 and $\beta$-thromboglobulin.

PF4 has been reported to inhibit the growth of melanoma and colon carcinoma in vivo, but not in vitro (Sharpe et al. (1990) J. Natl. Cancer Inst. 82:848–853; Maione et al. (1991) Cancer Res. 51:2077–2083).

It has been suggested that PF4 may inhibit growth of Kaposi sarcoma cells in vitro (Zucker et al. (1991) Proc. Soc. Exp. Biol. Med. 198:693–702; Miles et al. (1991) [abstract] VII International Conference on Aids (1991) Florence, Italy).

Hiti-Harper et al. (Science 199:99, 1978) report that PF4 inhibits collagenase derived from cultured human skin or human granulocytes.

Horton et al. (Biochim. Biophys. Acta 630:459, 1980) report that PF4 inhibits parathyroid hormone-stimulated $^{45}$Ca release from fetal rat bone in vitro.

SUMMARY OF THE INVENTION

In general, the invention features a method for inhibiting proliferation of osteoblasts in a mammal in need of such inhibition. The method entails administering PF4. In a preferred embodiment, the mammal is a human patient. In even more preferred embodiments, the human patient is suffering from osteosarcoma, the patient is suffering from ossifying fibroma, the patient is suffering from osteoid osteoma, the patient is suffering from fibrous dysplasia, and the patient is suffering from osteoporosis.

PF4 can be used to treat both diseases characterized by primary changes in osteoblastic cell function/activity (e.g., ossifying fibroma and fibrous dysplasia, osteoblastoma and osteoid osteoma, and osteosarcoma) and diseases or systemic conditions affecting bone in which abnormal osteoblastic cell function/activity is a secondary effect (e.g., acromegaly, hypercalcemia, primary or secondary hyperparathyroidism, hyperthyroidism, osteoporosis, or Paget's disease of bone). In addition, PF4 may be used to treat diseases associated with localized changes in bone metabolism in which abnormal osteoblastic cell function/activity contributes to pathogenic bone changes. For example, PF4 can be used to treat periodontal disease (localized, inflammation-induced bone loss), rheumatoid arthritis and osteoarthritis (localized, inflammation-induced bone loss) localized osteoporosis, mastocytosis, multiple myeloma, and bone metastases of various tumors.

Because of its inhibitory effect on osteoblastic cell proliferation, PF4 can be used to treat bone abnormalities associated with either undesired osteoblastic cell proliferation or undesired osteoblastic cell function or activity.

Natural or recombinant PF4 may be used in the method of the invention. In addition, biologically active fragments of PF4 having the ability to inhibit proliferation of osteoblasts may be used. Such biologically active fragments may be identified using the osteoblast proliferation assay described herein.

Other features and advantages of the invention will be apparent from the following description of the preferred embodiments thereof, and from the claims.

BRIEF DESCRIPTION OF THE DRAWINGS

FIGS. 3a and 3b are a set of graphs illustrating the effect of indomethacin on PF4-induced inhibition of proliferation of Saos-2 cells (FIG. 3a) and G-292 cells (FIG. 3b). Results are expressed as percentage of control (C) and represent the mean $\pm$S.E. of the mean from two experiments. In each experiment, points were tested in quadruplicates.

DESCRIPTION OF THE PREFERRED EMBODIMENT(S)

Figure 1A:
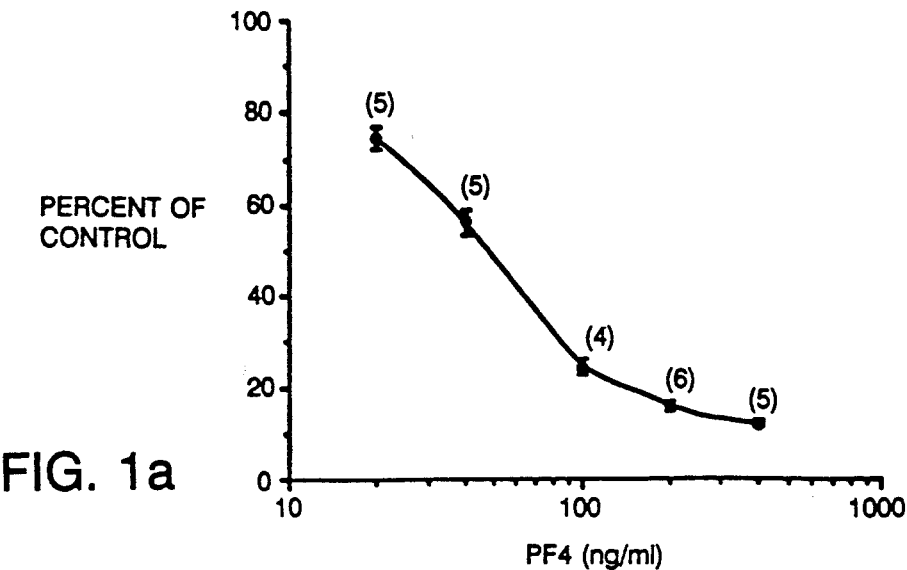
FIGS. 1a to 1c are a set of graphs illustrating the effect of PF4 on proliferations of G-292 cells grown in medium supplemented with 0.1% BSA (panel A), 2% fetal calf serum (panel B), or 0.1% BSA and 0.5 U/ml human alpha thrombin (panel C). Results are expressed as percentage of the maximum response under the culture condition tested and represent the mean $\pm$S.E. of the mean. The number of experiments is given in parenthesis above the specific points. In each experiment, points were tested in quadruplicates. Recent thymidine incorporation is plotted as a function of PF4 dose in ng/ml.

The experiments described below demonstrate that PF4 inhibits proliferation of two osteoblastic osteosarcoma cell lines (Saos-2 and G-292) in a dose-dependent manner. This inhibition was observed whether the cells were grown in serum-free media or were stimulated with either serum or thrombin. This direct effect on a osteoblastic cell line indicates that PF4 may be used to treat conditions associated with abnormal osteoblast activity. Further, it is known that cytokine- and hormone-stimulated resorption requires osteoblastic cells as mediators of the resorptive signal, even though osteoclasts are the terminal effector cells (Heersche (1989) in "Metabolic bone disease: Cellular and tissue mechanisms", CRC Press pp. 1–17) thus PF4 may be useful for treatment of disease conditions associated with inappropriate levels of osteoclast activity or proliferation.

The direct effect of PF4 against the osteosarcoma cells, the lack of PF4 toxic effects when given in vivo, and the immunoregulatory activities of PF4, all suggest that PF4 may be used to treat osteosarcoma in vivo.

The two human osteoblastic osteosarcoma cell lines Saos-2 (American Type Culture Collection, Bethesda, Md.; CRL 1423) (Rodan et al. (1987) Cancer Res. 47:4961-4966; Shupnik et al. (1982) J. Biol. Chem. 257:12161-12164) and G-292 (American Type Culture Collection, Bethesda, Md.; CRL 1423) were cultured in McCoy's 5a medium (GIBCO; Grand Island, N.Y.) supplemented with 10% (G-292) or 15% (Saos-2) fetal calf serum (FCS; GIBCO), in a humidified, 5% $CO_2$, 37° C. incubator. Cell proliferation was monitored by $^3$H-thymidine incorporation. The method is a slight modification of the procedure described by Tatakis et al. (Tatakis et al. (1989) Biochem. Biophys. Res. Commun. 164:119-127). Briefly, cells were seeded in 24-well flat bottom polystyrene dishes (Corning; Corning, N.Y.) ($0.9 \times 10^6$ cells/ml; 0.5 ml of cell suspension/well). After a 24 h incubation period in McCoy's 5a medium supplemented with 10% FCS, the cells were washed twice with McCoy's 5a medium and supplemented with 1 mg/ml BSA. The cells were then cultured in McCoy's 5a medium with BSA for 24 h. At the end of this 24 h period, the medium was removed and either McCoy's 5a medium with BSA or McCoy's 5a medium with BSA and human alpha thrombin (specific activity ca. 4,000 U/mg protein; Sigma Chemical Co., St. Louis, Mo.) or McCoy's 5a medium with FCS was placed in the wells (0.5 ml/well). PF4 (Calbiochem, San Diego, Calif.) was then added to the wells (in all experiments PF4 was added last, and at least 5 min after the addition of FCS or thrombin). The cells were then incubated for another 24-48 h. During the last three hours of this incubation period $^3$H-thymidine (1 $\mu$Ci/ml; ICN, Irvine, Calif.) was added to the medium. After the labeling period the cells were washed once with McCoy's 5a medium and then extracted with TCA. The acid-precipitable material was dissolved in KOH, neutralized with HCl, and counted in Ecoscint A (National Diagnostics; Manville, N.J.) scintillation fluid.

Figure 1B:
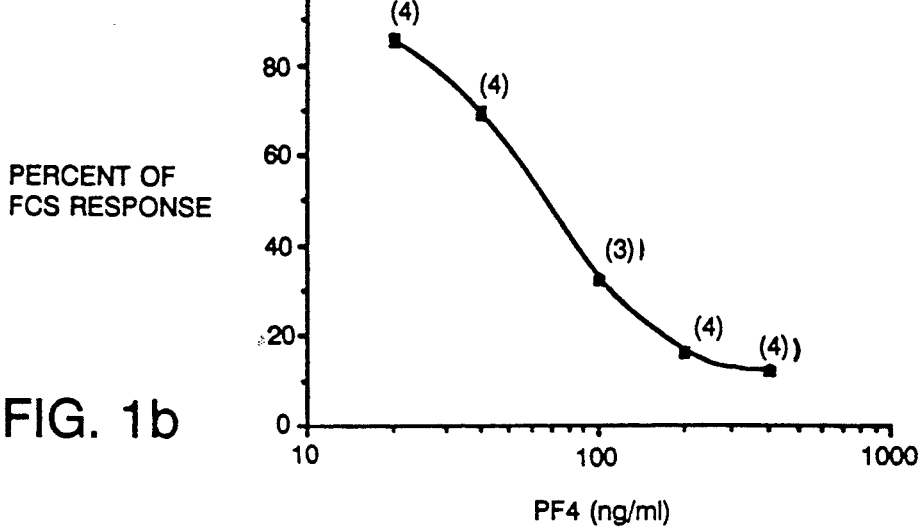
Figure 1C:
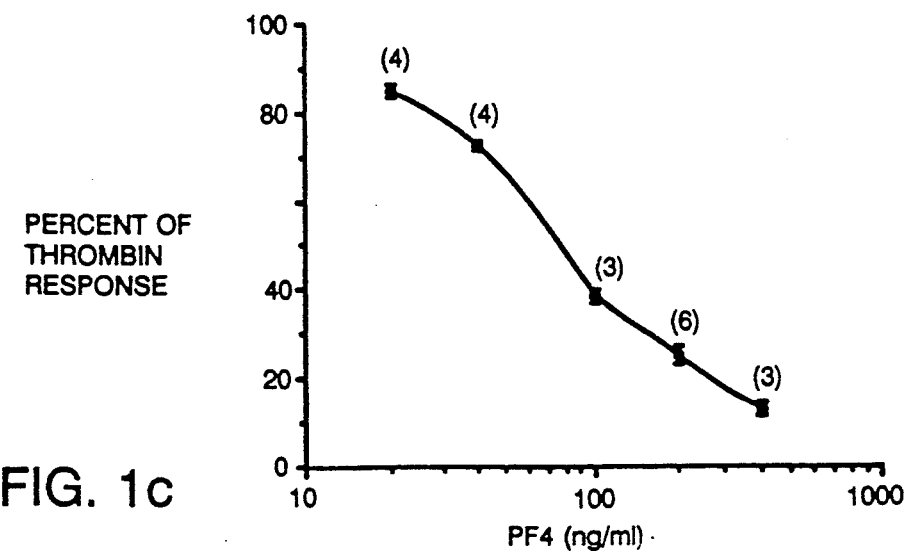

Referring to FIGS. 1a to 1c, PF4 inhibited proliferation of G-292 cells cultured in medium supplemented with 0.1% BSA (FIG. 1a), 2% FCS (FIG. 1b) or 0.1% BSA and 0.5 U/ml human alpha thrombin, FIG. 1c. PF4 was effective in this system at doses between 20 ng/ml and 2 $\mu$g/ml. In experiments with these cells, the average maximum response of the cells to 2% FCS and 0.5 U/ml thrombin was ~600% and ~750% of basal thymidine incorporation, respectively.

Figure 2A:
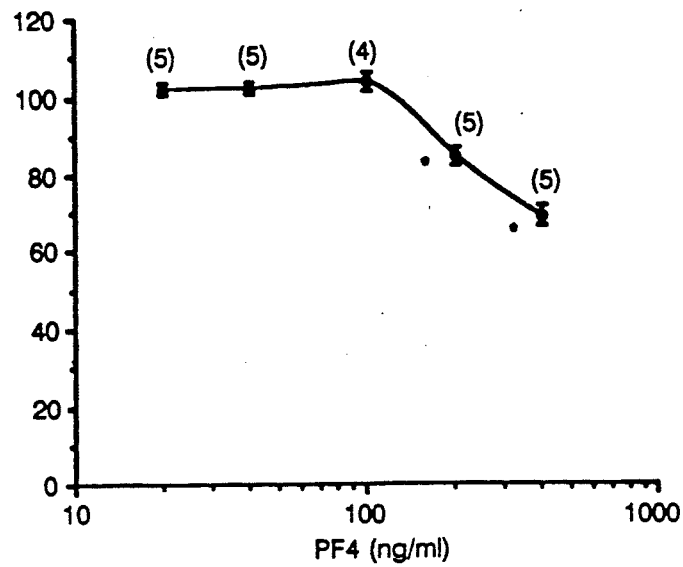
FIGS. 2a to 2c are a set of graphs illustrating the effect of PF4 on proliferations of Saos-2 cells grown in medium supplemented with 0.1% BSA (panel A), 2% fetal calf serum (panel B), or 0.1% BSA and 0.5 U/ml human alpha thrombin (panel C). Results are expressed as percentage of the maximum response under the culture condition tested and represent the mean $\pm$S.E. of the mean. The number of experiments is given in parenthesis above the specific points. In each experiment, points were tested in quadruplicates. Percent thymidine incorporation is plotted as a function of PF4 dose in ng/ml.
Figure 2B:
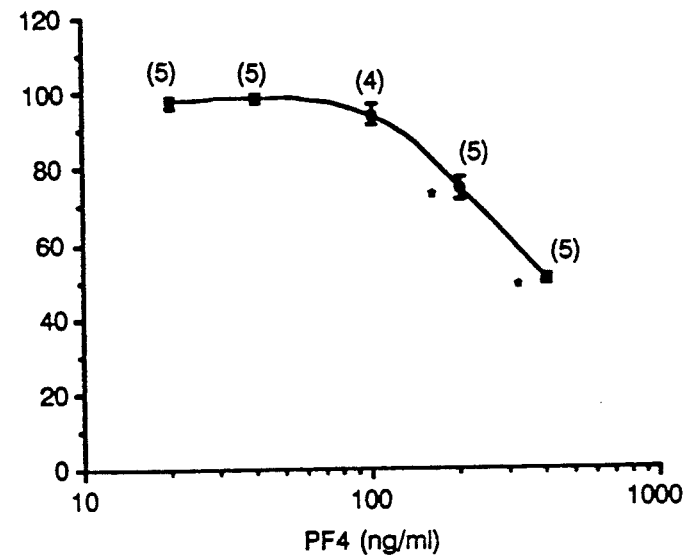
Figure 2C:
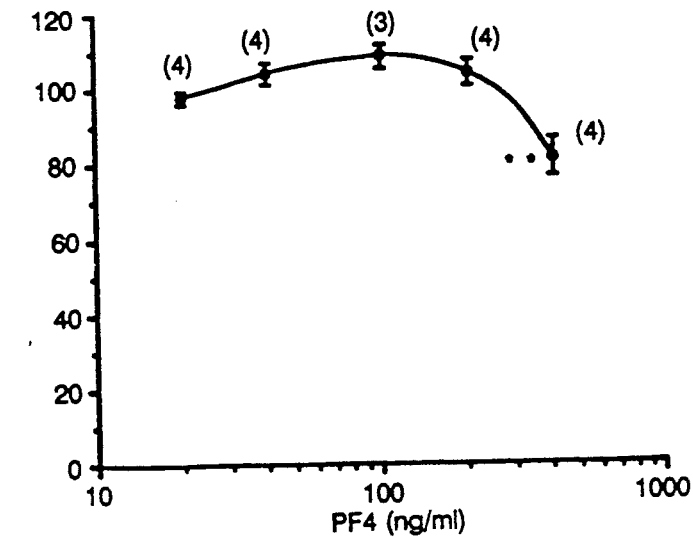

Referring to FIGS. 2a to 2c, PF4 inhibited proliferation of Saos-2 cells cultured in medium supplemented with 0.1% BSA (FIG. 2a), 2% FCS (FIG. 2b) or 0.1% BSA and 0.5 U/ml human alpha thrombin FIG. 2c. In experiments with these cells, the average maximum response of the cells to 2% FCS and 1.0 U/ml thrombin was ~1100% and ~370% of basal thymidine incorporation, respectively.

G-292 cells appeared to be much more susceptible to the action of PF4, compared to Saos-2 cells. A 100 ng/ml dose of PF4 caused a 75% inhibition of basal proliferation in G-292 cells (FIG. 1a), while it had no effect on Saos-2 cells (FIG. 2a). Thrombin-stimulated cells (FIGS. 1c and 2c) were the least affected by the inhibitory action of PF4, with the Saos-2 cells again being less susceptible. The degree of PF4-induced inhibition of FCS-stimulated cells (FIGS. 1b and 2b) was close to the degree of inhibition under basal conditions (FIGS. 1a and 2a) for both cell lines.

The doses at which PF4 effectively inhibited proliferation of either cell line are lower than those required for stimulation of elastase activity (Lonky et al. (1978) Biochem. Biophys. Res. Commun. 85:1113-1118), inhibition of collagenase (Hiti-Harper et al. (1978) Science 199:991-992), or inhibition of endothelial cell proliferation (Maione et al. (1990) Science 247:77-79; Sharpe et al. (1990) J. Natl. Cancer Inst. 82:848-853), and comparable to the doses required for reversal of immunosuppression (Katz et al. (1992) Int. Immunol. 4:183-190) and stimulation of monocyte (Deuel et al. (1981) Proc. Natl. Acad. Sci (USA) 78:4584-4587) or fibroblast chemotaxis (Senior et al. (1983) J. Cell Biol. 96:382-385). The PF4 doses effective against the osteosarcoma cells fall in the high range of normal PF4 values in plasma (mean $\pm SD = 13.9 \pm 6.1$ ng/ml) and within the PF4 levels that are theoretically possible at sites of activation of the coagulation cascade and release of platelet contents (Zucker et al. (1991) Proc. Soc. Exp. Biol. Med. 198:693-702; Files et al. (1981) Blood 58:607-618).

PF4 inhibited osteosarcoma cells grown either in the absence of any stimulus or in the presence of two differently acting stimulants, FCS and thrombin, suggesting that PF4 has direct effects on intrinsic mechanisms regulating the proliferation of osteosarcoma cells. Without being bound to any particular theory, the most likely mechanism of PF4 action would be the binding to a specific membrane receptor.

PF4 inhibited FCS- and thrombin-stimulated cells even though it was added five minutes after the addition of these agonists to the cells, suggesting that PF4 operates at a post-receptor stage of the stimulation process. The time element obtains particular significance when one considers that the thrombin-elicited intracellular signals occur within the first minute after addition of the enzyme to these cells (Tatakis et al. (1989) Biochem. Biophys. Res. Commun. 164:119-127; Tatakis et al. (1991) Biochem. Biophys. Res. Commun. 174:181-188). A separate set of experiments demonstrated that PF4 inhibits thrombin-stimulated cells to similar extent when it is added to the cells prior to the addition of thrombin.

A cytotoxicity assay demonstrated that the PF4-induced inhibition of osteosarcoma cell proliferation was not due to a cytotoxic effect of PF4 on these cells. Cytotoxicity was assessed using an LDH release assay. Briefly, cytotoxicity (LDH release) assay kits, based on a published procedure (Korzeniewski et al. (1983) J. Immunol. Methods 64:313-320), were obtained from Oxford Biomedical Research (Oxford, Mich.). For cytotoxicity experiments cells were seeded in 96-well flat bottom polystyrene dishes ($0.25 \times 10^6$ cells/ml; 0.2 ml of cell suspension/well). After 24 h growth period in McCoy's 5a medium supplemented with 10% FCS, the cells were washed twice with McCoy's supplemented with 1 mg/ml BSA. The cells were then cultured in McCoy's with BSA for 24 h. At the end of which the medium was removed and McCoy's with 2% FCS was placed in the wells (0.2 ml/well) with or without PF4 (six replicates/treatment group). The cells were then incubated for another 24 h. During the last three hours of this 24 h incubation period $^3$H-thymidine (1 $\mu$Ci/ml) was added to half the wells of each treatment group. The remaining three wells received lysing agent, in order to determine maximum LDH release values for each treatment group. After the 3 h period, a 100 $\mu$l aliquot was removed from each of the 6 wells and used in the LDH assay according to the manufacturer's instructions. The wells that had received $^3$H-thymidine were then treated as above for proliferation.

These experiments demonstrated that PF4 doses that caused significant inhibition of DNA synthesis had no significant effect on LDH release by Saos-2 or G-292 cells (Table 1).

TABLE 1

Effect of PF4 on osteosarcoma cell proliferation and viability

| Treatment | $^3$H-thymidine incorporation (% of maximum) | Cell viability (% of maximum LDH release) |
|---|---|---|
| G-292 cells: | | |
| 2% FCS | 100.0 ± 2.2 | 15.8 ± 3.4 |
| FCS + PF4 2 μg/ml | 8.3 ± 1.3[a] | 17.7 ± 3.8 |
| Saos-2 cells: | | |
| 2% FCS | 100.0 ± 1.0 | 10.9 ± 0.6 |
| FCS + PF4 2 μg/ml | 68.4 ± 2.4[a] | 8.8 ± 0.6 |

Results are the mean ± S.E. of the mean from two experiments, each performed in triplicates.
[a] $p < 0.001$ from FCS alone.

The fact that PF4 did not cause any cytotoxic effects on the osteosarcoma cells, as assessed by LDH release measurements, is consistent with the reported lack of cytotoxic effects of PF4 on endothelial cells (Maione et al. (1990) Science 247:77–79), and the lack of toxic effects when administered in vivo (Maione et al. (1991) Cancer Res. 51:2077–2083).

A separate set of experiments demonstrated that indomethacin did not effect PF4-induced inhibition of osteoblastic osteosarcoma cell proliferation, suggesting that this effect is independent of any PF4-elicited prostaglandin synthesis. Cell proliferation was measured as described above.

Referring to FIGS. 3a, Saos-2 cells were cultured with 0.1% BSA, 200 ng/ml PF4, 1% FCS, or 1% FCS and 200 ng/ml PF4 in the presence of 1 μM indomethacin (hatched bars) or solvent only (ethanol, 0.1% final concentration; solid bars). For each treatment, proliferation is expressed as a percentage of the control level.

Referring to FIGS. 3b, G-292 cells were cultured with 0.1% BSA (c), 200 ng/ml PF4, 0.5 U/ml human alpha thrombin (Thr), or 0.5 U/ml human alpha thrombin (Thr) and 200 ng/ml PF4 in the presence of 1 μM indomethacin (hatched bars) or solvent only (ethanol, 0.1% final concentration; solid bars). For each treatment, proliferation is expressed as a percentage of the control level.

Prostaglandins have direct effects on osteosarcoma cell proliferation (Ren et al. (1992) Calcif. Tissue Int. 50:372–377) and cytokines modulate osteoblastic cell growth through simulation of endogenous PG production (Tatakis et al. (1989) Biochem. Biophys. Res. Commun. 162:435–440). Indomethacin, a prostaglandin synthesis inhibitor, significantly inhibits the PF4-induced reversal of immunosuppression (Zucker et al. (1991) Proc. Soc. Exp. Biol. Med. 198:693–702; Katz et al. (1992) Int. Immunol. 4:183–190), suggesting that this immunoregulatory activity of PF4 requires prostaglandin production. However, indomethacin failed to alter the PF4-induced inhibition of osteoblast-like osteosarcoma cell growth. This suggests that the PF4 effect on osteosarcoma cells is prostaglandin-independent.

Naturally occurring or recombinant PF4 or fragments thereof can be used in the method of the invention. The production and cloning of PF4 have been described previously (Poncz et al., Blood 69:219, 1987; Cooke et al., Circulation 85:1102, 1992). These methods may be used to produce PF4 for use in the method of the invention. Methods for production of PF4 are also described in PCT Application WO 85/04397 (Oncogen, Inc.). Fragments of PF4 such as PF4 58–70 and PF4 47–70 (Rucinski et al., Thromb. Haemost. 63:493–498, 1990) and monomeric low-affinity PF4 (LAPF4), which is 50% homologous to PF4 and contains an α-helical C-terminus (Mayo, Biochem. 30:925–934, 1990), may be useful in the method of the invention. Other PF4 fragments potentially useful in the method of the invention are described by Rucinski et al. (Thrombosis and Haemostasis 63:493, 1990) and Maione et al. (Science 247:77, 1989).

Modified and mutant forms of PF4 may be useful in method of the invention. Such forms are described by Maione et al. (U.S. Pat. No. 5,086,164) and Maione (U.S. Pat. No. 5,112,946).

Various animal models are available for assessing the effectiveness of PF4 in the method of the invention. For example, canine models of osteosarcoma are commonly used. Ovariectomized rats provided a model of osteoporosis. Tumor necrosis factor or prostaglandins can be injected into the calvarium to provide a model of inflammation-induced resorption (e.g., as a model of periodontal disease).

Use

In administering PF4, conventional pharmaceutical or veterinary practice may be employed to provide suitable formulations or compositions for administration by any convenient means, for example, intravenous, subcutaneous, intramuscular, intraventricular, intracranial, intracapsular, intraspinal, intracisternal, intraperitoneal, or oral administration.

PF4 may also be administered by surgical implants which release formulations which include PF4.

Parenteral formulations may be in the form of liquid solutions or suspensions; for oral administration, formulations may be in the form of tablets or capsules.

Methods well known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes.

PF4 can be used as the sole active agent, or can be used in combination with other active ingredients, e.g., other compounds which could regulate osteoblast or osteoclast function.

The concentration of PF4 for administration in the method of the invention will vary depending upon a number of issues, including the dosage to be administered, and the route of administration.

In general terms, PF4 may be provided in an aqueous physiological buffer solution containing about 0.1 to 10% w/v compound for parenteral administration. The preferred dosage to be administered is likely to depend upon the type and extent of progression of the pathophysiological condition being addressed, the overall health of the patient, the make up of the formulation, and the route of administration.

What is claimed is:

1. A method for inhibiting proliferation of osteoblasts in a mammal in need of such inhibition comprising administering an effective amount of platelet factor 4 to said mammal.

2. The method of claim 1 wherein said mammal is a human.

3. The method of claim 2 wherein said human is suffering from osteosarcoma.

4. The method of claim 2 wherein said human is suffering from ossifying fibroma.

5. The method of claim 2 wherein said human is suffering from osteoid osteoma.

6. The method of claim 2 wherein said human is suffering from fibrous dysplasia.

7. The method of claim 2 wherein said human is suffering from osteoporosis.

8. The method for inhibiting proliferation of osteoblasts in a human suffering from osteoporosis comprising administering an effective amount of platelet factor 4 to said human.

* * * * *

UNITED STATES PATENT AND TRADEMARK OFFICE
CERTIFICATE OF CORRECTION

PATENT NO. : 5,304,542                                Page 1 of 2
DATED     : April 19, 1994
INVENTOR(S) : Dimitris N. Tatakis It is certified that error appears in the above-identified patent and that said Letters Patent is hereby corrected as shown below:

In the Abstract:

line 2, delete "inhibi7" and insert therefor -- inhibi- --;

line 5, delete "ossi7" and insert therefor -- ossi- --; and line 16, delete "peri7" and insert therefor -- peri- --.

Column 1, line 30, delete "99" and insert therefor -- 991 --;

Column 2, line 41, delete "FIG. 3a" and insert therefor -- Panel A --;

Column 2, line 42, delete "FIG. 3b" and insert therefor -- Panel B --;

Column 2, line 54, delete "a" and insert therefor -- an --;

Column 3, line 44, delete "FIG. 1c" and insert therefor -- (FIG 1c) --;

Column 3, line 53, delete "FIG. 2c" and insert therefor -- (FIG. 2c) --;

UNITED STATES PATENT AND TRADEMARK OFFICE
CERTIFICATE OF CORRECTION

PATENT NO. : 5,304,542

DATED : April 19, 1994

INVENTOR(S) : Dimitris N. Tatakis

It is certified that error appears in the above-identified patent and that said Letters Patent is hereby corrected as shown below:

Column 5, line 34, delete "FIGS." and insert therefor -- FIG. --;

Column 5, line 40, delete "FIGS." and insert therefor -- FIG. --; and

Column 6, line 56, delete "osteoclast" and insert therefor -- osteoblast --.

Claim 8, column 8, line 7, delete "The" and insert therefor -- A --.

Signed and Sealed this

Thirteenth Day of September, 1994

Attest:

BRUCE LEHMAN

*Attesting Officer*  *Commissioner of Patents and Trademarks*